United States Patent [19]

Abrams et al.

[11] Patent Number: 5,070,013

[45] Date of Patent: Dec. 3, 1991

[54] IMMUNOCHEMICAL ASSAY FOR HUMAN GRANULOCYTE-MACROPHAGE COLONY STIMULATING FACTOR

[75] Inventors: John S. Abrams, Belmont; Robert E. Van Dyke, Daly City, both of Calif.

[73] Assignee: Schering Corporation, Madison, N.J.

[21] Appl. No.: 201,068

[22] Filed: May 31, 1988

[51] Int. Cl.$^5$ .................. G01N 33/53; G01N 33/543; C07K 15/14; C12N 15/00
[52] U.S. Cl. .................................. 435/7.5; 435/7.9; 435/7.94; 435/718; 435/21; 435/28; 435/172.2; 435/240.24; 435/975; 436/501; 436/518; 436/536; 436/548; 436/808; 436/824; 530/387; 530/413; 530/809; 935/95; 935/106; 935/110
[58] Field of Search .................. 435/7, 18, 21, 28, 30, 435/172.2, 240.27, 810, 7.1, 7.5, 7.9, 7.92, 7.94, 975; 436/501, 518, 547, 548, 808, 824, 536; 530/387, 412, 413, 809; 935/95, 106, 110

[56] References Cited

U.S. PATENT DOCUMENTS

| | | | |
|---|---|---|---|
| 4,486,530 | 12/1984 | David et al. | 436/529 |
| 4,562,003 | 12/1985 | Lewicki | 435/7 |
| 4,642,334 | 2/1987 | Moore et al. | 435/7 |
| 4,810,643 | 3/1989 | Souza | 530/351 |
| 4,851,341 | 7/1989 | Hopp et al. | 530/387 |

OTHER PUBLICATIONS

Conlon et al., Biological Abstracts, vol. 85, Abstract No. 48134, 1987.
Metcalf, Science, 229:16-22, Jul. 1985.
Groopman, Cell, 50:5-6, Jul. 3, 1987.
Clark et al., Science, 236:1229-1237, Jun. 1987.
Brennan et al., Science, 229:81-83, Jul. 1985.
Miyajima et al., The EMBO Journal, 5(6):1193-1197, 1986.

Primary Examiner—Esther L. Kepplinger
Assistant Examiner—Florina B. Hoffer
Attorney, Agent, or Firm—Stephen C. Macevicz

[57] ABSTRACT

Monoclonal antibodies and compositions thereof are provided for detecting, measuring, and immunopurifying human GM-CSF.

8 Claims, 1 Drawing Sheet

IMMUNOCHEMICAL ASSAY FOR HUMAN GRANULOCYTE-MACROPHAGE COLONY STIMULATING FACTOR

FIELD OF THE INVENTION

The invention relates generally to monoclonal antibodies and their associated hybridomas, and more particularly, to monoclonal antibodies specific for human granulocyte-macrophage colony stimulating factor (GM-CSF).

BACKGROUND

Circulating blood cells are constantly replaced by newly developed cells. Replacement blood cells are formed in a process termed hematopoiesis which involves the production of at least eight mature blood cell types within two major lineages: (1) myeloid which includes red blood cells (erythrocytes), macrophages (monocytes), eosinophilic granulocytes, megakaryocytes (platelets), neutrophilic granulocytes, basophilic granulocytes (mast cells); and (2) lymphoid which includes T lymphocytes, and B lymphocytes, Burgess and Nicola, *Growth Factors and Stem Cells* (Academic Press, New York, 1983). Much of the control of blood cell formation is mediated by a group of interacting glycoproteins termed colony stimulating factors (CSFs). These glycoproteins are so named because of the in vivo and in vitro assays used to detect their pressence. Techniques for the clonal culture of hematopoietic cells in semisolid culture medium have been especially important in the development of in vitro assays. In such cultures, individual progenitor cells (i.e., cells developmentally committed to a particular lineage, but still capable of proliferation) are able to proliferate to form a colony of maturing progeny in a manner which is believed to be essentially identical to the comparable process in vivo. The role of CSFs in hematopoiesis is the subject of many recent reviews, e.g. Metcalf, *The Hemopoietic Colony Stimulating Factors* (Elsevier, New York, 1984); Metcalf, *Science*, Vol. 229, pgs. 16-22 (1985); Nicola et al., *Immunology Today*, Vol. 5, pgs. 76-80 (1984); Whetton et al., *TIBS*, Vol. 11, pgs. 207-211 (1986), Clark and Kamen, *Science*, Vol. 236, pgs. 1229-1237 (1987) and Sachs, *Science*, Vol. 238, pgs. 1374-1379 (1987).

The detection, isolation and purification of these factors is extremely difficult, being frequently complicated by the complexity of the biological fluids they are typically located in, and their very low concentrations. As more CSFs become available, primarily through molecular cloning, interest has heightened in finding clinical applications for them. Because of physiological similarities to hormones (e.g., soluble factors, growth mediators, action via cell receptors), potential uses of CSFs have been analogized to the current uses of hormones, e.g. Dexter, *Nature*, Vol. 321, pg. 198 (1986). Their use has been suggested for several clinical situations where the stimulation of blood cell generation would be desirable, such as for rehabilitative therapy after chemotherapy or radiation therapy of tumors, treatment of myeloid hypoplasias, treatment of neutrophil deficiency, treatment to enhance hematopoietic regeneration following bone marrow transplantation, and treatment to increase host resistance to established infections, e.g. Dexter (cited above), Metcalf, *Science* (cited above), and Clark and Kamen (cited above). Recently, recombinant human GM-CSF has been shown to produce a dose-dependent increases in circulating leukocyte count in severely leukopenic AIDS patients, Groopman, *Cell*, Vol. 50, pgs. 5-6 (1987).

CSFs are also believed to play a role in the development and progression of myeloid leukemias. Myeloid leukemias are clonal neoplasms of granulocyte-macrophage precursor cells, which fall into two major groups—chronic myeloid leukemia (CML) and acute myeloid leukemia (AML). CML is characterized by expansion in the marrow of the granulocyte-monocyte population at all stages of maturation with massive enlargement of hematopoietic populations in the spleen and blood. While chemotherapy is successful in reducing the excessive size of the leukemic cell populations conventional regimens have not succeeded in preventing terminal acute transformation (of progressively higher proportions of cells into immature or abnormal forms) or in extending the life spans of afflicted patients, Metcalf (cited above, 1984).

AML is characterized by an accumulation of immature granulocyte-monocyte blast cells with often little or no evidence of maturing granulocyte-monocyte cells. The disease primarily involves the bone marrow, and spleen enlargement usually is only moderate. Total blood nucleated cells may or may not be elevated but there is a high proportion of immature blast cells associated with relatively few mature cells. There is usually an associated anemia, thrombocytopenia and a relative absence in the marrow and peripheral blood of mature granulocytes and monocytes. Death usually results from uncontrollable hemorrhage or overwhelming infections, Metcalf (cited above, 1984).

It is believed that both forms of leukemia are driven by abnormal production of, or responsiveness to, colony stimulating factors, particularly GM-CSF. In particular, it has been shown that leukemic cells from some AML patients are capable of autonomous in vitro proliferation because they express GM-CSF constitutively, and that such autonomous proliferation can be inhibited by the addition of GM-CSF neutralizing antiserum, Young et al., *Blood*, Vol. 68, pgs. 1178-1181 (1986).

It is believed that myeloid leukemias, in particular AML, may be treated by blocking the ability of GM-CSF to stimulate cell growth. Blocking agents can be derived from monoclonal antibodies specific for human GM-CSF.

Such monoclonal antibodies have other uses, including detection, measurement, and purification of GM-CSF. An important aspect of any therapy involving drugs is the ability to predict and/or monitor concentration levels in the blood or other patient body fluids. Monoclonal antibodies are widely used for this purpose, e.g. Springer, ed., *Hybridoma Technology in the Biosciences and Medicine* (Plenum Press, N.Y., 1985); and U.S. Pat. Nos. 4,562,003; 4,486,530; and 4,255,329.

In the production of genetically engineered proteins such as human GM-CSF, separation of the expressed protein from the transformed host cells and/or their culture supernatants is a major problem. Frequently separation procedures involve one or more passes of crude material through immunoadsorbent columns. Monoclonal antibodies specific for the protein to be purified are crucial elements of such columns. Such monoclonal antibodies can also be used to measure the degree of purification achieved by a particular protocol, e.g. by "Western" blot analysis, Burnette, *Anal. Biochem.*, Vol. 112, pgs. 195-203 (1981).

From the foregoing, it is evident that the availability monoclonal antibodies specific for human GM-CSF could facilitate the medical and veterinary applications of GM-CSF by providing alternative methods to bioactivity measurements for its detection, purification, and measurement.

SUMMARY OF THE INVENTION

The invention provides compounds, compositions, and kits useful for the detection, and measurement of human GM-CSF. The compounds and compositions are derived from hybridomas producing monoclonal antibodies specific for human GM-CSF. The compounds and compositions of the invention include the hybridomas themselves derivative and parental hybridomas thereof, monoclonal antibodies produced by the hybridomas, heavy chain and light chain variable region polypeptides thereof, and other fragments thereof, such as half-molecules comprising a light chain joined to a heavy chain by natural disulfide bonds, Fab fragments, F(ab)$_2$ fragments, Fv fragments, and the like, and useful conjugates of such monoclonal antibodies and fragments, e.g. enzyme-antibody conjugates, and the like. The invention also includes methods of using the above compounds and compositions to detect, purify, and measure the concentration of human GM-CSF, and kits for practicing such methods. In particular, the invention includes hybridomas BVD2-5A2.4, BVD2-23B6.4, and BVD2-21C11.3, their derivatives and parental hybridomas, and their respective monoclonal antibodies and products derived therefrom. These hybridomas are deposited with the American Type Culture Collection (ATCC) in Rockville, Md., under accession numbers HB9567, HB9568, and HB9569, respectively.

Compositions of the invention also include messenger RNA (mRNA) extracted from hybridomas BVD2-5A2.4, BVD2-23B6.4, and BVD2-21C11.3. Such mRNAs are useful in cloning and expressing fragments of the respective antibodies in bacteria, yeast, or other hosts.

Antibodies comprise an assembly of polypeptide chains linked together by disulfide bridges. Two major polypeptide chains, referred to as the light chain and the heavy chain, make up all major structural classes (isotypes) of antibody. Both heavy chains and light chains are further divided into subregions referred to as variable regions and constant regions. Heavy chains comprise a single variable region and three or more different constant regions, and light chains comprise a single variable region (different from that of the heavy chain) and a single constant region (different from those of the heavy chain). The variable regions of the heavy chain and light chain are primarily responsible for the antibody's binding specificity.

As used herein, the term "heavy chain variable region" means a polypeptide (1) which is from 110 to 125 amino acids in length, and (2) whose amino acid sequence corresponds to that of a heavy chain of a monoclonal antibody of the invention, starting from the heavy chain's N-terminal amino acid. Likewise, the term "light chain variable region" means a polypeptide (1) which is from 95 to 115 amino acids in length, and (2) whose amino acid sequence corresponds to that of a light chain of a monoclonal antibody of the invention, starting from the light chain's N-terminal amino acid.

The terms Fab, Fc, F(ab)$_2$, and Fv are employed with their standard immunological meanings, e.g. Klein, *Immunology* (John Wiley, New York, 1982) or Parham, Chapter 14, in Weir, ed. *Immunochemistry*, 4th Ed. (Blackwell Scientific Publishers, Oxford, 1986).

As used herein the term "monoclonal antibody" refers to homogenous populations of immunoglobulins which are capable of specifically binding to human GM-CSF.

As used herein the term "binding composition" means a composition comprising two polypeptide chains (1) which, when operationally associated, assume a conformation having high binding affinity for human GM-CSF, and (2) which are derived from a hybridoma producing monoclonal antibodies specific for human GM-CSF. The term "operationally associated" is meant to indicate that the two polypeptide chains can be positioned relative to one another for binding by a variety of means, including by association in a native antibody fragment, such as Fab or Fv, or by way of genetically engineered cysteine-containing peptide linkers at the carboxyl termini. Normally, the two polypeptide chains correspond to the light chain variable region and heavy chain variable region of a monoclonal antibody specific for human GM-CSF.

DETAILED DESCRIPTION OF THE INVENTION

Figure 1:
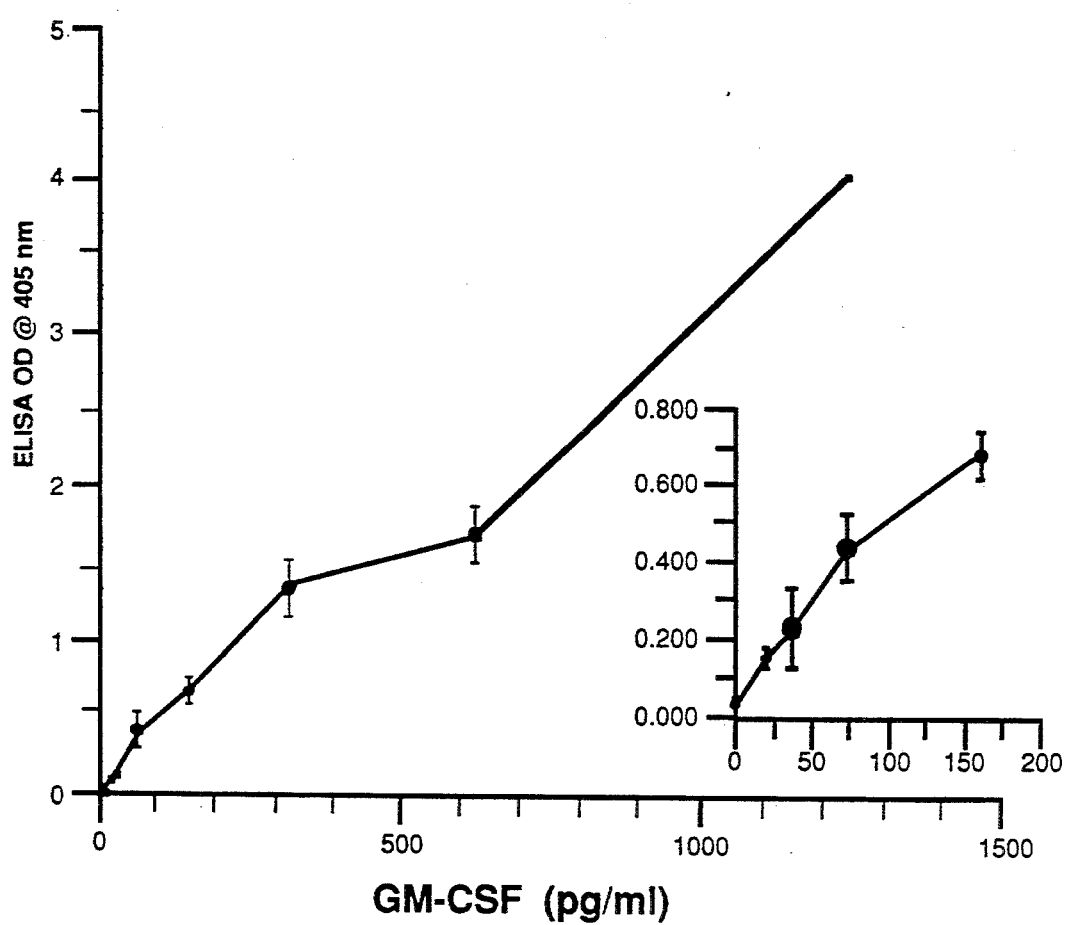
FIG. 1 illustrates data from several ELISA assays of human GM-CSF at different concentrations.

Hybridomas of the invention were produced by standard techniques. Spleen cells were removed from a male Lewis rat immunized intraperitoneally with unglycosylated human GM-CSF using standard protocols. The isolated spleen cells were fused with mouse myeloma cells, P3X63-Ag8.653 (ATCC CRL 1580), in a 1:1 ratio using polyethylene glycol. The hybridomas of the invention were selected by indirect ELISA, inhibition of GM-CSF in a bioassay, and ability to immunoprecipitate radiolabeled GM-CSF. The hybridomas were cloned by limiting dilution.

The hybridomas are stored (e.g. $-70°$ C. in culture medium with 10% DMSO) and cultured using standard mammalian cell culture techniques (e.g., RPMI 1640 with 10% fetal bovine serum, supplemented with 1 mM glutamine and 50 mM 2-mercaptoethanol). Antibodies are recovered from hybridoma culture medium using standard protein purification techniques, e.g. Tijssen, *Practice and Theory of Enzyme Immunoassays* (Elsevier, Amsterdam, 1985). Many references are available for guidance in applying any of the above techniques, e.g. Kohler et al., *Hybridoma Techniques* (Cold Spring Harbor Laboratory, New York, 1980); Tijssen, *Practice and Theory of Enzyme Immunoassays* (Elsevier, Amsterdam 1984); Hurrell, *Monoclonal Hybridoma Antibodies: Techniques and Applications* (CRC Press, Boca Raton, FL, 1982); and the like.

The use and generation of fragments of antibodies is also well known, e.g. Fab fragments: Tijssen, *Practice and Theory of Enzyme Immunoassays* (Elsevier, Amsterdam, 1985); and Fv fragments: Hochman et al., *Biochemistry*, Vol. 12, pgs. 1130–1135 (1973), Sharon et al., *Biochemistry*, Vol. 15, pgs. 1591–1594 (1976) and Ehrlich et al., U.S. Pat. No. 4,355,023; and antibody half molecules: Auditore-Hargreaves, U.S. Pat. No. 4,470,925. Moreover, such compounds and compositions of the invention can be used to construct bispecific antibodies by known techniques, e.g., via further fusions of hybridomas (i.e. to form so-called quadromas), Reading, U.S. Pat. No. 4,474,493; or via chemical reassociation of half molecules, Brennan et al., *Science*, Vol. 229, pgs. 81-83 (1985). Accordingly, these references are incorporated by reference.

Antibodies and antibody fragments characteristic of hybridomas of the invention, can also be produced by recombinant means by extracting messenger RNA, constructing a cDNA library, and selecting clones which encode segments of the antibody molecule, e.g. Wall et al., *Nucleic Acids Research*, Vol. 5, pgs. 3113-3128 (1978); Zalsut et al., *Nucleic Acids Research*, Vol. 8, pgs. 3591-3601 (1980); Cabilly et al., *Proc. Natl. Acad. Sci.*, Vol. 81, pgs. 3273-3277 (1984); Boss et al., *Nucleic Acids Research*, Vol. 12, pgs. 3791-3806 (1984); Amster et al., *Nucleic Acids Research*, Vol. 8, pgs. 2055-2065 (1980); and Moore et al., U.S. Pat. No. 4,642,334. In particular, such techniques can be used to produce interspecific monoclonal antibodies, wherein the binding region of one species is combined with non-binding region of the antibody of another species, e.g. Liu et al., *Proc. Natl. Acad. Sci.*, Vol. 84, pgs. 3439-3443 (1987). Accordingly, U.S. Pat. No. 4,642,334 is incorporated by reference.

Uses of monoclonal antibodies for purification and measurement are well known, e.g. affinity chromatography: *Affinity Chromatography: Principles and Methods* (Pharmacia, Orebro, Sweden, 1979); Secher et al., *Nature*, Vol. 285, pgs. 446-450 (1980), and U.S. Pat. No. 4,423,147; and European patent application 0190711 (Aug. 13, 1986); and immunoassay techniques: Tijssen (cited above); U.S. Pat. No. 4,486,530; and burnette (cited above). Affinity chromatography can be used to purify human GM-CSF by extracting it from a sample, such as a culture supernatant of cells transformed or transfected with a human GM-CSF expression vector. Such a purification process is referred to herein as an immunopurification process. Typically, it involves covalently attaching a monoclonal antibody specific for human GM-CSF to a solid phase support (referred to herein as an "immunoadsorbent") which is placed in a column or chamber through which the sample is passed. Human GM-CSF from the sample preferentially binds to the binding sites of the attached monoclonal antibodies, while the rest of the material from the sample is washed from the column or chamber. The human GM-CSF is then eluted from the immunoadsorbent by standard techniques, e.g. low pH, high salt concentration, or the like.

"Two site" or "sandwich" immunoassays are the preferred immunoassays of the invention, e.g. as disclosed in U.S. Pat. No. 4,486,530. Accordingly, this patent is incorporated by reference. Such assays entail the use of two different sets of anti-GM-CSF antibodies, at least one of which consists of a monoclonal antibody of the invention. Antibodies from one of the two sets are attached to the surface of a solid phase support. The attached antibodies are then exposed to a sample suspected of containing human GM-CSF. The GM-CSF molecules bind to the attached antibodies. Next, the second set of antibodies is applied to the bound GM-CSF, and the antibodies bind to one or more antigenic determinants distinct from that (or those) to which the first set of antibodies is (or are) bound. The GM-CSF is then detected by an indirect or direct signal generating means associated with the second set of antibodies. For example, the antibodies can be directly conjugated to a signal generating moiety, such as an enzyme, rare earth chelator, or an organic dye. Or, they can be indirectly linked to one or more signal generating moieties via additional antibodies, or high affinity complexes, such as avidin- or streptavidin-biotin complexes. Quantitative measures of human GM-CSF concentration are made by comparing the signal generated by the sample to signals generated by human GM-CSF standards containing known concentrations of human GM-CSF.

The invention includes kits of reagents for use in immunoassays, particularly sandwich immunoassays. Such kits include (1) a solid phase support, (2) a first antibody which is monoclonal and which is capable of binding to a first antigenic determinant of human GM-CSF, (3) a second antibody selected from the group consisting of a monoclonal antibody capable of binding to a second antigenic determinant of human GM-CSF and a polyclonal antibody specific for human GM-CSF (referred to herein as a "polyclonal antibody composition"), and (4) a signal generation means associated with one of the three antibodies. Depending on the particular embodiment, kits may include a selection of two of the three anti-GM-CSF antibody types, either a monoclonal antibody specific for a first antigenic determinant and a monoclonal antibody specific for a second antigenic determinant, or a monoclonal antibody specific for a first or second antigenic determinant and a polyclonal antibody composition. The antibodies may be in solution or in lyophilized form. One of the sets of antibodies may come pre-attached to the solid support, or may be applied to the surface of the solid support when the kit is used. The signal generating means may come pre-associated with one of the two antibody types, or may require combination with one or more components, e.g. buffers, antibody-enzyme conjugates, enzyme substrates, or the like, prior to use. Many types of signal generating means are available and could make up one or more components of a kit. Various signal generating means are disclosed by Tijssen (cited above). Kits of the invention may also include additional reagents, e.g. blocking reagents for reducing nonspecific binding to the solid phase surface, washing reagents, enzyme substrates, and the like. The solid phase surface may be in the form of microtiter plates, microspheres, or the like, composed of polyvinyl chloride, polystyrene, or the like materials suitable for immobilizing proteins. Such materials having solid phase surfaces are referred to herein as "support means". Preferably, an enzyme which catalyzes the formation of a fluorescent or colored product is a component of the signal generating means. More preferably, the enzyme is selected from the group consisting of peroxidase, alkaline phosphatase, and beta-galactosidase. Substrates and reaction conditions for these enzymes are well known in the art, e.g. Tijssen (cited above).

EXAMPLES

The following examples serve to illustrate the present invention. Selection of particular reagents, concentrations, temperatures, and values of other variable parameters and materials are only to exemplify application of the present invention and are not to be considered as limitations thereof.

EXAMPLE I

Detection of Human GM-CSF Produced by *Saccharomyces cerevisiae*

Methods for producing recombinant human GM-CSF in yeast is described by Miyajima et al., *EMBO J.*, Vol. 5, pgs. 1193-1197 (1986). Media from stationary phase cultures of *Saccharomyces cerevisiae* harboring an expression plasmid for human GM-CSF is concentrated approximately 40-fold using Centricon 10 concentrators (Amicon Corp., Danvers, MA). The recovered samples are diluted 1:1 with SDS sample buffer containing 0.0625M Tris-HCl, pH 6.8, 2% SDS, 10% glycerin, and 5% beta-mercaptoethanol, and boiled for 5 min. The samples are loaded on an SDS 5-15% continuous gradient polyacrylamide gel with a discontinuous buffer system, Laemmli, *Nature*, Vol. 227, pgs. 680-685 (1970). After electrophoresis, the protein is transferred electrophoretically to nitrocellulose membranes (BA 85, Schliecher and Schuell, Keene, NH) by overnight transfer at 0.2 amps in 20 mM Tris base, 150 mM glycine, in 20% methanol, at 4° C.

Immunoblotting of nitrocellulose-immobilized protein is carried out as follows; all incubation and washing steps are performed at 4° C. The membranes are blocked in 100 ml of 0.5% bovine serum albumin in PBS. The first-stage antibodies are dilutions of the rat anti-GM-CSF hybridoma supernatants in PBS containing 0.1% bovine serum albumin and 05.% Tween 20. The membranes are incubated in 10 ml of these solutions for 2 hours. The membranes are washed in 3 changes of 100 ml of the PBS-BSA-Tween buffer for 20 min each. A 50 μl vol of $^{125}$I-labelled sheep anti-rat Ig, in 50 ml of PBS-BSA-Tween is used as the second-stage labelled antibody. The blots are incubated for 2 hours, followed by another washing step as described above. They are then dried briefly and exposed to X-Ray film (NIF New RFX, Fuji Photo Film Co., Japan).

EXAMPLE II

Two-site Sandwich Assay of Recombinant Human GM-CSF Produced by *Escherichia coli*

Microtiter plates were coated with 100 μl of monoclonal antibody from BVD2-23B6.4 at a concentration of 10 μg/ml in phosphate buffered saline (PBS) by incubation for 2 hours at 37° C. The microtiter plates were washed with PBS containing 0.05% Tween 20, and serial dilutions of purified recombinant human GM-CSF (0-1250 pg/ml) were added and allowed to stand at room temperature for 2 hours, after which the plate was washed with PBS containing 0.05% Tween. Bound human GM-CSF was detected by first adding nitroiodophenyl (NIP)-derivatized monoclonal antibodies from BVD2-21C11.3 to the microtiter plate (100 μl at 100 μg/ml, incubated for 2 hours at 37° C.), washing, and then adding a rat anti-NIP monoclonal antibody conjugated to horseradish peroxidase. A signal was generated by peroxidase oxidation of 2,2'-azino-bis(3-ethylbenzthiazoline-6-sulfonic acid) (ABTS), which results in a chromogenic product. The NIP-derivatized antibodies were obtained by first forming a NIP succinimide ester using standard techniques (e.g. Pierce Chemical Company Handbook and Catalog, 1985-1986), and then reacting the NIP succinimide ester with the antibodies, e.g. in PBS at pH 7.2. The assay could also be readily carried out using an avidin-biotin or streptavidin-biotin signal generation system.

FIG. 1 illustrates data from the immunoenzymetric two-site sandwich assay for human GM-CSF using monoclonal antibodies produced by BVD2-21C11.3 and BVD2-23B6.4. As shown by the data this embodiment of the invention is capable of detecting human GM-CSF at levels of 20 pg/ml or less.

The descriptions of the foregoing embodiments of the invention have been presented for purpose of illustration and description. They are not intended to be exhaustive or to limit the invention to the precise forms disclosed, and obviously many modifications and variations are possible in light of the above teaching. The embodiments were chosen and described in order to best explain the principles of the invention and its practical application to thereby enable others skilled in the art to best utilize the invention in various embodiments and with various modifications as are suited to the particular use contemplated. It is intended that the scope of the invention be defined by the claims appended hereto.

Applicants have deposited hybridomas BVD2-5A2.4, BVD2-23B6.4, and BVD2-21C11.3 with the American Type Culture Collection, Rockville, MD, USA (ATCC), under accession numbers HB9567, HB9568, and HB9569, respectively. These deposits were made under conditions as provided under ATCC's agreement for Culture Deposit for Patent Purposes, which assures that the deposits will be made available to the US Commissioner of Patents and Trademarks pursuant to 35 USC 122 and 37 CFR 1.14, and will be made available to the public upon issue of a U.S. patent, which requires that the deposits be maintained. Availability of the deposited strains is not to be construed as a license to practice the invention in contravention of the rights granted under the authority of any government in accordance with its patent laws.

We claim:

1. A method of detecting the presence of human granulocyte-macrophage colony stimulating factor (GM-CSF) in a sample suspected of containing human GM-CSF, the method comprising the steps of:

providing a first monoclonal antibody specific for a first antigenic determinant on human GM-CSF, the first monoclonal antibody being produced by a hybridoma selected from the group consisting of BVD2-5A2.4 (ATCC accession no. HB9567), BVD2-23B6.4 (ATCC accession no. HB9568), BVD2-21C11.3 (ATCC accession no. HB9569), and derivative or parental hybridomas thereof;

providing a second monoclonal antibody specific for a second antigenic determinant on human GM-CSF, the second antigenic determinant being different from the first antigenic determinant and the second monoclonal being produced by a hybridoma selected from the group consisting of BVD2-5A2.4 (ATCC accession no. HB9567), BVD2-23B6.4 (ATCC accession no. HB9568), BVD2-21C11.3 (ATCC accession no. HB9569), and derivative or parental hybridomas thereof;

providing a signal generating means capable of being operationally associated with either the first monoclonal antibody or the second monoclonal antibody to produce a signal whose intensity is related to the amount of either the first monoclonal antibody or the second monoclonal antibody, respectively;

attaching either the first monoclonal antibody or the second monoclonal antibody to a support means to form an antibody-support conjugate;

contacting the sample with the antibody-support conjugate so that human GM-CSF in the sample binds to the antibody-support conjugate;

contacting the first monoclonal antibody operationally associated with the signal generating means with the human GM-CSF bound to the antibody-support conjugate, provided that the antibody-support conjugate includes the second antibody or;

contacting the second antibody operationally associated with the signal generating means with the human GM-CSF bound to the antibody-support conjugate, provided that the antibody-support conjugate includes the first monoclonal antibody;

measuring the signal generated by the signal generating means; and associating said signal with the presence and/or amount of human GM-CSF in the sample.

2. A monoclonal antibody specific for granulocyte-macrophage colony stimulating factor, the monoclonal antibody being produced by a hybridoma selected from the group consisting of BVD2-5A2.4 (ATCC accession no. HB9567), BVD2-23B6.4 (ATCC accession no. HB9568), BVD2-21C11.3 (ATCC accession no. HB9569), and derivative or parental hybridomas thereof.

3. A hybridoma selected from the group consisting of BVD2-5A2.4 (ATCC accession no. HB9567), BVD2-23B6.4 (ATCC accession no. HB9568), BVD2-21C11.3 (ATCC accession no. HB9569), and derivative or parental hybridomas thereof.

4. A kit for detecting the presence of human GM-CSF in a sample suspected of containing human GM-CSF, the kit comprising:

a first monoclonal antibody specific for a first antigenic determinant on human GM-CSF, the first monoclonal antibody being produced by a hybridoma selected from the group consisting of BVD2-5A2.4 (ATCC accession no. HB9567), BVD2-23B6.4 (ATCC accession no. HB9568), BVD2-21C11.3 (ATCC accession no. HB9569), and derivative or parental hybridomas thereof;

a second monoclonal antibody specific for a second antigenic determinant on human GM-CSF, the second antigenic determinant being different from the first antigenic determinant and the second monoclonal antibody being produced by a hybridoma selected from the group consisting of BVD2-5A2.4 (ATCC accession no. HB9567), BVD2-23B6.4 (ATCC accession no. HB9568), BVD2-21C11.3 (ATCC accession no. HB9569), and derivative or parental hybridomas thereof;

a support means; and a signal generating means.

5. The kit of claim 4 wherein said signal generation means comprises an enzyme operationally associated with said first monoclonal antibody.

6. The kit of claim 5 wherein said enzyme is selected from the group consisting of peroxidase, betagalactosidase, and alkaline phosphatase.

7. The kit of claim 4 wherein said signal generation means comprises said first monoclonal antibody derivatized with biotin and streptavidin or avidin operationally associated with a plurality of enzymes of a fluorescent organic molecules.

8. An immunopurification process for extracting human GM-CSF from a sample containing human GM-CSF wherein the sample is passed through an immunoadsorbent column comprising a monoclonal antibody produced by a hybridoma selected from the group consisting of BVD2-5A2.4 (ATCC accession no. HB9567), BVD2-23B6.4 (ATCC accession no. HB9568), BVD2-21C11.3 (ATCC accession no. HB9569), and derivative or parental hybridomas thereof.

* * * * *